US011453634B2

(12) United States Patent
Cavani et al.

(10) Patent No.: US 11,453,634 B2
(45) Date of Patent: Sep. 27, 2022

(54) PRODUCTION OF CARBOXYLIC ACIDS FROM VICINAL DIOLS

(71) Applicants: NOVAMONT S.P.A., Novara (IT); MATRICA S.P.A., Porto Torres (IT); ALMA MATER STUDIORUM—Universita' di Bologna, Bologna (IT)

(72) Inventors: Fabrizio Cavani, Modena (IT); Andrea Vassoi, Gaggio Montano (IT)

(73) Assignees: NOVAMONT S.P.A., Novara (IT); MATRICA S.P.A., Porto Torres (IT); ALMA MATER STUDIORUM—Universita' di Bologna, Bologna (IT)

( * ) Notice: Subject to any disclaimer, the term of this patent is extended or adjusted under 35 U.S.C. 154(b) by 0 days.

(21) Appl. No.: 16/765,983

(22) PCT Filed: Nov. 22, 2018

(86) PCT No.: PCT/EP2018/082219
§ 371 (c)(1),
(2) Date: May 21, 2020

(87) PCT Pub. No.: WO2019/101856
PCT Pub. Date: May 31, 2019

(65) Prior Publication Data
US 2020/0325095 A1  Oct. 15, 2020

(30) Foreign Application Priority Data

Nov. 22, 2017  (IT) .................. 102017000133748

(51) Int. Cl.
*C07C 51/245* (2006.01)
*B01J 31/28* (2006.01)
*C11C 3/00* (2006.01)
C07C 53/126 (2006.01)
C07C 55/18 (2006.01)

(52) U.S. Cl.
CPC ............ *C07C 51/245* (2013.01); *B01J 31/28* (2013.01); *C11C 3/006* (2013.01); *C07C 53/126* (2013.01); *C07C 55/18* (2013.01)

(58) Field of Classification Search
CPC ..... C07C 51/245; C07C 53/126; C07C 55/18; B01J 31/28; C11C 3/006
See application file for complete search history.

(56) References Cited

U.S. PATENT DOCUMENTS 4,792,620 A * 12/1988 Paulik .................. B01J 31/0231
                                                            560/232
8,440,859 B2 * 5/2013 Dubois .................. C07C 51/377
                                                            562/606
9,359,280 B2 * 6/2016 Lemaire ................ C07D 317/12

9,796,648 B2 * 10/2017 Ye ......................... B01J 23/8877
2008/0183013 A1 * 7/2008 Dubois ..................... C07C 45/52
                                                                562/538
2012/0302778 A1 * 11/2012 Bieser ....................... C07C 51/09
                                                                554/132
2012/0323028 A1 * 12/2012 Bieser .................... C07C 51/245
                                                                554/136
2014/0357880 A1 * 12/2014 Brandhorst ............. C07C 51/21
                                                                554/113
2015/0210623 A1     7/2015 Lemaire et al.
2017/0057898 A1 *  3/2017 Ye ............................ C07C 47/22

FOREIGN PATENT DOCUMENTS

DE           4308120 A1 *  9/1993  .............. B01J 23/72
WO        2011080296 A1    7/2011
WO        2017202955 A1   11/2017
WO    WO-2017202955 A1 * 11/2017  .............. C07C 51/25

OTHER PUBLICATIONS

Norskov et al, Nature Chemistry, Towards the Computational Design of Solid Catalysts, 2009, 1, pp. 37-46. (Year: 2009).*
R. Arandiyan et al., 26 Brazilian Journal of Chemical Engineering, 63-74 (2009) (Year: 2009).*
G. Dodekatos et al., 9 ChemCatChem, 610-619 (2017) (Year: 2017).*
A. Cimino et al., 47 Adv. Catal., 141-306 (2002) (Year: 2002).*
T. Franken et al., 382 Journal of Catalysis, 385-394 (2020) (Year: 2020).*
T. Reina et al., 40 International Journal of Hydrogen Energy, 1782-1788 (2015) (Year: 2015).*
H. Chen et al., 6 Journal of Materials Chemistry A, 11129-11133 (2018) (Year: 2018).*
J. Vieten et al., 7 Energy Technology, 131-139 (2019) (Year: 2019).*
B. Reddy et al., 47 Catalyst Reviews, 257-296 (2005) (Year: 2005).*
Z. Jiang et al., 4 ACS Sustainable Chemistry & Engineering (2016) (Year: 2016).*
S. Liu et al., 4 ACS Catalysis, 2226-2230 (2014) (Year: 2014).*
G. Yang et al., 283 Chemical Engineering Journal, 759-767 (2016) (Year: 2016).*
D. Roy et al., 1 ACS Catalysis, 548-551 (2011) (Year: 2011).*
A. Moreira et al., 144 Fuel Processing Technology, 170-180 (2016) (Year: 2016).*
P. Amaniampong et al., 20 Green Chemistry, 2730-2741 (2018) (Year: 2018).*
P. Amaniampong et al., 306 Catalysis Today, 171-182 (2018) (Year: 2018).*

(Continued)

*Primary Examiner* — Alexander R Pagano
(74) *Attorney, Agent, or Firm* — Silvia Salvadori, P.C.; Silvia Salvadori

(57) ABSTRACT

A process of preparation of carboxylic acids by oxidative cleavage of compounds having substituted or non-substituted, linear or branched, saturated or unsaturated alkyl chains containing at least one vicinal diol or an epoxide in the presence of an oxidant comprising molecular oxygen and a heterogeneous catalyst comprising a copper oxide.

7 Claims, No Drawings

(56) References Cited

OTHER PUBLICATIONS

Kulik A. et al., "Insights into gold-catalyzed synthesis of azelaic acid", Green Chemistry, vol. 16, No. 4, Jan. 1, 2014, pp. 1799-1806.
Search Report and Written Opinion of PCT/EP2018/082219 dated Jan. 31, 2019.
Reply to Search Report of Italian patent application No. 102017000133748 dated Nov. 22, 2018.

* cited by examiner

PRODUCTION OF CARBOXYLIC ACIDS FROM VICINAL DIOLS

This application is a U.S. national stage of PCT/EP2018/082219 filed on 22 Nov. 2018, which claims priority to and the benefit of Italian Application No. 102017000133748 filed on 22 Nov. 2017, the contents of which are incorporated herein by reference in their entireties.

The project which led to the invention was financed by the Bio Based Industries Joint Undertaking Public-Private Partnership as part of the European Union Horizon 2020 research and innovation programme under Grant Agreement No. 669029.

This invention relates to a process for the preparation of carboxylic acids by the oxidative cleavage of vicinal diols and/or epoxides in the presence of catalysts containing copper oxides.

STATE OF THE ART

Carboxylic acids can be prepared by processes of various kinds. High yields of saturated monocarboxylic and dicarboxylic acids can be obtained from renewable sources and with low environmental impact, for example through processes of the oxidative cleavage of unsaturated fatty acids, their derivatives and their natural sources such as animal and vegetable oils and fats.

The main renewable source of monocarboxylic and dicarboxylic acids is oleic acid. The oxidative cleavage of oleic acids mainly yields pelargonic acid and azelaic acid, which can in turn be used in the polymer industry as bio-monomers for the production of polyamides and polyesters, and find application also in the pharmaceutical and cosmetics industries, or as biolubricants.

Some of the processes of oxidative cleavage of unsaturated fatty acids, their derivatives or vegetable oils containing them mentioned above are described in EP 666 838 B1, EP 1 926 699 B1, WO 2008/138892, WO 2011/080297 and WO 2011/080296. The said processes provide for the unsaturations present in the fatty acids to undergo a first catalytic oxidation step which results in the production of vicinal diols; subsequently the two hydroxides of the vicinal diols undergo a second oxidation step with oxygen (or gas containing oxygen) which leads to the formation of monocarboxylic acids and dicarboxylic acids. The second oxidation step requires the addition of a second catalyst, different from that in the first step and typically belonging to the group of cobalt compounds, generally used in aqueous solution.

These processes make it possible to achieve a selective conversion of oleic acid, its derivatives or triglycerides containing it to azelaic acid or its derivatives and pelargonic acid, with high selectivity as regards other dicarboxylic and monocarboxylic acids of different chain length.

In the continuous process described in WO 2011/080297 for example the second oxidation step is carried out continuously on methyl esters of 9,10-dihydroxystearic acid in a CSTR reactor of the jet-loop type, using cobalt acetate and oxygen-enriched air (P=20 bar) at a temperature of 60° C.; high molar yields of pelargonic acid and azelaic acid are obtained after 3.5 hours' reaction.

In WO 2011/080296 pelargonic acid and azelaic acid are selectively prepared from vegetable oils containing hydroxylated triglycerides, at 70° C. and using the same catalyst. The ratio by weight between by-products (short chain acids) and desired products (C9 chain acids) is in fact very low; examples show a ratio between C8/C9 monocarboxylic acids of around 3% when operating continuously and around 8% in batch systems.

The preparation of carboxylic acids through the oxidation of vicinal diols is also described in U.S. Pat. No. 3,711,523, a process which uses catalysts based on Co(II) salts in the presence of organic peroxides.

U.S. Pat. No. 4,606,863 describes a process for the preparation of carboxylic acids with air or oxygen in which transition metal compounds, preferably cobalt, manganese, cerium and nickel, are used in the presence of a bromine or chlorine compound.

However, the catalysts used in the process described above are potentially toxic. They are furthermore typically used in the form of an aqueous solution and are therefore difficult to separate from the reaction medium. For this reason they contaminate the product and limit possibilities for recovery and recycling, having an adverse effect on the economics of the process.

US 2015/0210623 describes a process for the preparation of carboxylic acids by oxidative cleavage of diols or epoxides using supported metals or supported metal hydroxides. Oxidative cleavage is catalysed by $Ru(OH)_x/Al_2O_3$, at temperatures above 120° C.; long reaction times (15-18 h) and a dilution with organic solvent are needed to separate the catalyst from the product.

There is therefore a need to identify processes which use catalytic systems having reduced toxicity and which can also be readily recovered from the reaction medium and reused, without thereby reducing selectivity for the products of interest.

DESCRIPTION OF THE INVENTION

The process of the oxidative cleavage of vicinal diols or epoxides according to the invention uses catalysts based on copper oxide which have lower intrinsic toxicity than the catalysts commonly used industrially. These catalysts are also in a form which enables them to be more easily separated from the reaction environment, consequently reducing the possibilities for contamination of the product in comparison with the homogeneous catalysts commonly used.

Unexpectedly, the copper oxide based catalysts according to the invention also have high selectivity for the products of interest, at least comparable to that achieved with the catalysts currently in use, the term "selectivity" meaning the ratio between the number of moles of desired products and the number of moles of oxidation by-products.

The object of this invention is therefore a process for the preparation of carboxylic acids by the oxidative cleavage of at least one vicinal diol or an epoxide in the presence of an oxidising agent comprising molecular oxygen and a heterogeneous catalyst comprising a copper oxide.

The copper oxide catalyst preferably does not include manganese.

The diols and/or epoxides subjected to the oxidative cleavage process according to the invention are compounds having substituted or non-substituted, linear or branched, saturated or unsaturated alkyl chains containing at least two vicinal hydroxyl groups or at least one epoxy group; among these, saturated fatty acids or their derivatives containing at least two vicinal hydroxyl groups or at least one epoxy group are preferred. Internal diols and/or internal epoxides are preferred, i.e. compounds whose vicinal hydroxyl groups or epoxy groups do not involve the first carbon atom of the alkyl chain.

Compounds containing vicinal diols or epoxides prepared from unsaturated fatty acids or their derivatives are preferred. From these it is possible to obtain both monocarboxylic acids and dicarboxylic acids or their derivatives through oxidative cleavage.

Unsaturated fatty acids which are suitable for preparing the said vicinal diols and/or epoxides are monounsaturated and/or polyunsaturated carboxylic acids such as for example 9-tetradecenoic (myristoleic) acid, 9-hexadecenoic (palmitoleic) acid, 9-octadecenoic (oleic) acid, 12-hydroxy-9-octadecenoic (ricinoleic) acid, 9-eicosenoic (gadoleic) acid, 13-docosenoic (erucic) acid, 15-tetracosenoic (nervonic) acid, 9,12-octadecadienoic (linoleic) acid, and 9,12,15-octadecatrienoic (linolenic) acid. Monounsaturated carboxylic acids are preferred; in particular oleic acid, from the oxidative cleavage of which mainly azelaic acid and pelargonic acid are obtained.

Other examples of suitable compounds are dimers and trimers of unsaturated carboxylic acids.

Mixtures of unsaturated carboxylic acid, such as for example those present in vegetable oils such as soya oil, olive oil, castor oil, sunflower oil, peanut oil, maize oil, palm oil, jatropha oil, cuphea oil, oils from Cardueae such as *Cynara cardunculus, Silybum marianum* or *Carthamus tinctorius*, oils from Brassicaceae such as *Crambe abyssinica, Brassica carinata, Brassica napus* (colza), *Lesquerella*, and other oils having a high monounsaturated acid content are also advantageously used.

According to this invention, "derivative" of a saturated or an unsaturated carboxylic acid means an unsaturated carboxylic acid whose carboxyl group forms an ester bond (e.g. through reaction with an alcohol), an amide bond, a nitrile bond (e.g. by reaction with an amine), a thioester bond (e.g. through reaction with a thiol), etc. Said derivative may be of natural or synthetic origin.

Preferably, said derivatives are esters of unsaturated carboxylic acids with monoalcohols and/or polyalcohols.

In the case of derivatives of the ester type the carboxylic group may be attached to monoalcohols or polyalcohols. Preferred monoalcohols comprise C1-C9 alkyl groups; more preferred are methyl, ethyl, propyl and butyl alcohols. One example of a preferred polyalcohol is glycerol.

Methyl and ethyl esters of unsaturated carboxylic acids are particularly advantageous as starting materials for the present process, in particular those obtained through the transesterification of methanol and ethanol with the triglycerides present in sunflower oil having a high oleic acid content.

One embodiment of the invention therefore relates to a process for the preparation of carboxylic acids through the oxidative cleavage of at least one vicinal diol (or an epoxide) prepared from an alkyl ester of an unsaturated carboxylic acid in the presence of an oxidising agent comprising molecular oxygen and a heterogeneous catalyst comprising a copper oxide.

Monoglycerides, diglycerides and triglycerides of unsaturated carboxylic acids or mixtures thereof, whether synthetic or natural, are also particularly advantageous as starting materials for the process for preparing the diols and/or epoxides according to the invention. Among the latter the triglycerides present in vegetable oils or their mixtures are particularly preferred. By vegetable oils are meant both the unmodified product of pressing, or an oil which has undergone chemical/physical modifications such as for example purification or hydrogenation treatments or enzyme enrichment treatments. Examples of preferred vegetable oils are: soya oil, olive oil, castor oil, sunflower oil, peanut oil, maize oil, palm oil, jatropha oil, cuphea oil, oils from Brassicaceae such as *Crambe abyssinica, Brassica carinata, Brassica napus* (colza), oils from Cardueae such as *Cynara cardunculus* (cardo), *Silybum marianum, Carthamus tinctorius, Lesquerella*, and other oils having a high monounsaturated acid content. The use of sunflower oil and thistle oils is particularly preferred.

Another embodiment of the invention therefore relates to a process for the preparation of carboxylic acids through the oxidative cleavage of at least one vicinal diol (or an epoxide) prepared from one or more glycerides of unsaturated carboxylic acids, preferably a triglyceride containing at least one unsaturated carboxylic acid, in the presence of an oxidising agent comprising molecular oxygen and a heterogeneous catalyst comprising a copper oxide. Vicinal diols (or epoxides) prepared from mixtures of triglycerides, such as vegetable oils are preferred.

Said vicinal diol and the said epoxide can for example be prepared by the oxidation of unsaturated molecules with the help of oxidising agents selected from osmium tetroxide, permanganates, hydrogen peroxide, alkyl-hydroperoxides and percarboxylic acids such as performic acid, peracetic acid or perbenzoic acid.

Said oxidation may be advantageously performed in the presence of a catalyst activating oxidation of the olefinic double bond.

Said catalyst advantageously belongs to the group of transition elements and contains one or more elements selected from Fe, Mn, Mo, Nb, Os, Re, Ti, V, W, Zr and their acids, alkaline salts and complexes, in homogeneous or heterogeneous phase, possibly in a supported or nanostructured form. The use of tungstic acid and/or its derivatives, such as phosphotungstic acid, is particularly preferred.

According to a preferred aspect, the process according to the invention therefore comprises an optional step of preparing a vicinal diol or epoxide through the oxidation of unsaturated compounds with an oxidising agent and a catalyst activating the oxidation reaction of the olefinic double bond, before the oxidative cleavage (preparation step).

The oxidising agent used to perform said preparation step is preferably an aqueous solution of hydrogen peroxide in concentrations of from 30 to 80% by weight, preferably from 40 to 70% and even more preferably from 49 to 65%.

The catalyst preferably comprises tungstic acid and/or its derivatives, such as phosphotungstic acid; it is present for example in quantities of from 0.03% to 3% in moles, preferably from 0.05% to 1.8% in moles and even more preferably from 0.06% to 1.5% in moles with respect to the total moles of unsaturated compounds.

The preparation reaction is preferably performed at atmospheric pressure or in a slight vacuum and advantageously at temperatures of from 40 to 80° C.

Preferred examples of preparation are described in EP 666 838 B1, EP 1 926 699 B1, WO 2008/138892, WO 2011/080297 and WO 2011/080296, incorporated here for reference. In these documents, said preparation step corresponds to process step a).

At the end of the said optional preparation step a mixture comprising vicinal diols and/or epoxides and any solvents, catalysts and unreacted starting material is obtained.

Said mixture is passed to an optional purification step and then to the oxidative cleavage step.

Said optional purification step, which is designed to separate the diol (and/or epoxide) from any solvents, catalysts and unreacted starting material present in the mixture can be carried out according to known methods. For example it may comprise one or more operations selected from decanting, centrifuging, washing with solvents, drying or combinations thereof, meaning by "drying" the at least partial removal of the solvent possibly present by known techniques, for instance evaporation.

In a preferred form of the process, the mixture obtained at the end of the preparation step is fed directly to the oxidative cleavage step without the need for purification treatments. This embodiment, which is preferably used when the diol is prepared in the presence of hydrogen peroxide and tungstic acid or phosphotungstic acid, allows an advantageous reduction of the reaction time thanks to the greater reactivity of the mixture, with a significant increase in reaction yield.

The oxidative cleavage reaction of at least one vicinal diol or at least one epoxide according to the invention is performed in the presence of an oxidising agent comprising molecular oxygen or a gas containing molecular oxygen, for example air or enriched air.

As far as the oxidative cleavage reaction catalyst is concerned, this comprises a copper oxide and may for example be used in the form of a sheet, particles or spheres typically having dimensions of from 1 to 4 mm.

By "copper oxide" is meant a copper oxide in a supported form, a mixed oxide or mixtures thereof.

The support for the said copper oxide is selected from the group comprising: alumina, silica, $CeO_2$, $TiO_2$, $ZrO_2$, MgO, polycrystalline or amorphous oxide substrates, carbon, amorphous charcoal, inorganic-organic sol-gel matrices, zeolites, aluminosilicates, alkaline earth carbonates, montmorillonites, polymer matrices, polyfunctional resins, ion exchange resins, ceramic supports, or mixtures of two or more of these.

The use of copper oxides supported on silica, alumina, $CeO_2$, $TiO_2$ or mixtures thereof is preferred. The use of copper oxides supported on silica, alumina or their mixture is even more preferred.

Typically, the said copper oxide in supported form comprises copper oxide in a quantity of from 1 to 25% by weight, preferably from 5 to 20% by weight. The use of copper oxide supported on silica and alumina is particularly preferred; copper oxide supported on silica is even more preferred, advantageously in quantities from 1 to 20% by weight.

Examples of catalysts suitable for use in the process according to the invention are CuO supported on $Al_2O_3$ containing 13% by weight of CuO (Sigma Aldrich product), CuO supported on $Al_2O_3$ containing 15-20%, CuO supported on $SiO_2$ containing 5-10% by weight of CuO.

By "mixed oxide" is meant an oxide also comprising one or more metal elements other than copper in addition to the cupric and/or cuprous ion. Said elements are for example selected from iron, zinc, aluminium, nickel, manganese and their mixtures; iron, zinc, aluminium, nickel and their mixtures being preferred. Said mixed oxide is advantageously in the form of spinel.

A preferred mixed oxide is copper ferrite ($CuFe_2O_4$), or solid solutions between two metal oxides of Cu and Fe, of variable composition. Examples of suitable copper ferrites have a Cu/Fe atomic ratio of 1/2 or below, e.g. 1/4 or 1/6, the ferrites having a Cu/Fe atomic ratio of 1/4 being more preferred.

A mixture comprising copper oxide and copper ferrite is particularly preferred.

As it will be obvious from the examples shown below, in addition to being characterised by low toxicity and insolubility in the reaction environment, these catalyst systems surprisingly provide catalytic performance which is comparable to that of the homogeneous systems currently in industrial use, as regards selectivity, making it possible to obtain low ratios between by-products and desired products. They also have high activity, which can be determined as the conversion of reagent taking place in a particular period of time and under specific reaction conditions. In addition to a higher catalytic activity, the heterogeneous catalytic systems based on copper oxides of the invention have unexpectedly demonstrated a considerably lower leaching compared to supported metal copper or supported copper hydroxides, especially when the support material is alumina or silica.

One aspect of the invention therefore relates to the use of a supported copper oxide, a mixed oxide comprising copper oxide or a mixture thereof as an oxidative cleavage catalyst for at least one vicinal diol or epoxide, in the presence of an oxidising agent comprising molecular oxygen, for the preparation of carboxylic acids.

As it is known, catalytic activity may be further increased for example by acting on the reaction temperature, the contact time and the specific surface area of the support, which should be sufficient to ensure adequate dispersion of the catalyst.

According to a preferred aspect of the invention, the catalyst comprises copper oxide, mixed oxides or mixtures thereof in quantities of generally from 0.05 to 20%, preferably from 0.1 to 10%, more preferably from 0.1 to 2%, even more preferably from 0.3 to 1.5% in moles with respect to the total moles of diol and/or epoxide. The quantity of catalyst may vary within this range depending upon the nature of the catalyst, its surface area and the concentration of catalyst with respect to any support.

The catalyst, whether a copper oxide in supported form or a mixed oxide, may be prepared using techniques known to those skilled in the art.

For example, supported oxides may be prepared by finely dispersing a metal salt onto a support by deposition, adsorption from a solution, co-precipitation or impregnation, for example through incipient wetness impregnation.

Mixed oxides may be prepared by precipitation from aqueous solutions of salts or complexes of Cu such as $CuCl_2$, $Cu(NO_3)_2 \cdot xH_2O$, $CuSO_4 \cdot xH_2O$, Cu oxalate, Cu acetate, or others.

The step of preparing the catalyst may be performed separately from the oxidative cleavage process according to the present invention and may take place in a preliminary step thereof.

The process according to the invention may optionally be performed in the presence of one or more catalysts in addition to copper oxide, belonging to the group of transition elements, for example selected from Ce, Cr, Co, Cu, Mn, Mo, Re, Os, V and W and their acids, alkaline salts and complexes; catalysts comprising W are preferred.

According to one aspect of the process the oxidative cleavage reaction is performed in the presence of the catalyst used for preliminary preparation of the diol (and/or the epoxide).

Advantageously, at the end of the oxidative cleavage reaction the catalyst is recovered and at least partially recycled in subsequent oxidative cleavage reactions. In general the oxidative cleavage reaction according to the present invention may be performed in one or more suitable pieces of apparatus such as for example stirred reactors, continuous and semi-continuous reactors, external recycling reactors (jet loop type), or fixed bed, mobile bed, entrained flow and fluidised bed or airlift reactors.

In the case of stirred reactors, in particular, stirring of the medium helps to determine the rate of diffusion of the oxidising agent and the amount of contact between the diol (and/or epoxide) and the oxygen. Depending upon the volume and the configuration of the reactor, stirring speeds of from 100 to 1200 rpm, more particularly from 100 to 1000 rpm, may be used. The stirring speed for the system preferably lies from 300 to 800 rpm.

The process of the invention is carried out at temperatures advantageously higher than 45 and lower than 120° C., preferably from 50 to 100° C.

Holding temperatures below 100° C. makes it possible to reduce degradation phenomena in the starting material, the carboxylic acids produced and the catalyst, which can be more readily reused. Temperatures below 45° C. may determine mixing problems related to the viscosity of the reaction mixture. In particular the temperature of the oxidative cleavage reaction varies according to the composition of the starting material and is advantageously from 55 to 90° C., even more advantageously from 60 to 85° C.

The optional preliminary step of diol (and/or epoxide) preparation is advantageously performed at temperatures from 55 to 80° C.

The oxidative cleavage reaction is advantageously carried out at moderate partial pressures of oxygen, with obvious advantages from the point of view of industrial production. This is preferably carried out at a pressure of from 1 bar to 50 bar, preferably from 5 bar to 30 bar with air or oxygen. In accordance to an embodiment of the invention, the molecular oxygen pressure is <25 bar, preferably <20 bar, more preferably <15 bar. According to a specific embodiment of the invention wherein the oxidative cleavage reaction is carried out in the presence of copper ferrites, the molecular oxygen pressure is preferably from 1 bar to 30 bar, more preferably <25 bar.

The time for the oxidative cleavage reaction according to the invention depends upon the composition of the starting material, operating conditions (for example temperature and pressure), and the nature and dimensions of the reactor used, and is typically from 60 minutes to 24 hours, for example from 2 to 8 hours.

The process may be controlled in a known way, for example by measuring the internal pressure of the reactor and interrupting the reaction when a particular quantity of oxygen has been absorbed.

As an alternative, it is possible to monitor the course of the reaction by sampling and analysing the composition of the reaction mixture.

The theoretical quantity of oxygen required to complete the reaction may be easily determined on the basis of the composition of the starting material, for example by analysing the quantity of diol and/or epoxide in moles.

The process according to the invention is advantageous since it can be performed in the absence of any inorganic or organic solvent, i.e. in the presence of solvent amounts of 10% by weight or less or preferably of 5% or less and more preferably of 3% by weight or less with respect to the weight of the reaction mixture.

The reaction mixture may contain solvent deriving from the preliminary step of diol preparation, for example water.

The quantity of solvent present in the course of the oxidative cleavage step is advantageously less than 50% by weight with respect to the reaction mixture, preferably less than 10%, thus making it possible to reduce reaction volumes.

According to an aspect of the invention, the oxidative cleavage reaction is performed in the absence of organic solvent.

According to an aspect of the invention, the oxidative cleavage reaction is performed in the presence of supported copper oxides and in the absence of water.

At the end of the reaction the catalyst may be readily recovered using known techniques, such as for example centrifugation, filtration or settling, and reused several times, with or without preliminary purification and/or regeneration treatments. In accordance with an embodiment of the invention, the catalyst is subjected to a regeneration step before being recycled according to known techniques. For example, said regeneration step comprises one or more operations selected from washing, drying, calcination and hydrogenation. Washing is advantageously preformed with organic solvents such as ketones; calcination is preferably performed at temperatures of from 300° C. to 750° C., more preferably of above 400° C. Preferred calcination temperatures vary according to the substrate, e.g. supported copper oxides are advantageously calcined at temperatures of 500° C. or above, while the mixed oxides of the invention are preferably calcined at temperatures from 400° C. to 500° C.

In a preferred embodiment, the process for the preparation of carboxylic acids according to the invention comprises one or more further steps in which the catalyst is separated from the oxidative cleavage product, for example by means of one or more filtration or settling operations, optionally purified and recycled in a subsequent oxidative cleavage step.

The oxidative cleavage product so obtained comprises carboxylic acids or their derivatives, which may be further separated by means of conventional techniques, for example on the basis of their solubility in water and/or by means of distillation processes. Separation of the carboxylic acids obtained from the present process may for example be helped by subjecting the reaction product to one or more hydrolysis and/or esterification reactions.

As an alternative, the oxidative cleavage product may be used as such or comprise the starting material for the preparation of lubricating oils or biodiesel or as an intermediate in the preparation of polymers.

The process according to the invention may be carried out in batch mode, continuous mode or semi-continuous mode, e.g. by continuous addition of oxidising agent and removal of inert gas.

The following examples illustrate the invention in greater detail.

EXAMPLES

The starting material used in each example (crude diol), containing triglycerides comprising 9,10-dihydroxystearic acid, was prepared through the dihydroxylation reaction of high-oleic sunflower oil according to the process described in Example 2 in WO 2011/080296 (step a).

In each example approximately 15 g of starting material were charged into a 100 mL batch autoclave together with catalyst (1% by weight) at a temperature of 25, without using organic solvents. The autoclave was pressurised with 25 bar of O2 (99.999% purity) and the reaction was carried out for 5 hours at a constant temperature of 80° C. with stirring (500 rpm).

At the end of the reaction the products were discharged from the reactor and separated from the catalyst by centrifuging at 4500 rpm for 10 minutes.

The reaction products were analysed by gas chromatography, after being converted into derivatives through a transmethylation reaction with $BF_3$/MeOH.

The transmethylation was carried out in accordance with the method illustrated below: $BF_3$ in MeOH (2.8 mL), toluene (1 mL) and 2,2'-dimethoxypropane (150 μL) were added to a known quantity of reaction mixture (approximately 0.1 g) and internal standard solution containing 10-undecenoic acid and nonadecanoic acid (approximately 0.4 μL). After incubation in a stove for 1 hour at 80° C. the sample was cooled; 1 mL of solution was taken and transferred into a flask, to which were subsequently added 1 mL of water and 1 mL of chloroform. The solution was shaken and centrifuged at 4000 rpm for 5 minutes. The aqueous phase comprising the glycerine deriving from the reaction was separated from the organic phase comprising the methyl esters.

The organic phase was then dehydrated with $Na_2SO_4$ and injected into the GC-FID.

Yield was calculated by determining the quantity by weight of product of interest (on the basis of the calibration lines for the mono- and dicarboxylic acids), in relation to the quantity which could be theoretically obtained from the starting oil assuming complete conversion of the unsaturated components.

Starting from a sunflower oil having a high oleic acid content (HOSO) having the acid composition shown in the table 1 it is possible to calculate a maximum theoretical pelargonic acid content of 37% by weight and a maximum azelaic acid content of 48% by weight for the product from oxidative cleavage.

TABLE 1

| Fatty acid composition of high oleic sunflower oil used for preparation of the diol | |
|---|---|
| Fatty acid | % p |
| Palmitic acid (C16:0) | 4.2 |
| Palmitoleic acid (C16:1) | 0.1 |
| Stearic acid (C18:0) | 2.8 |
| Oleic acid (C18:1) | 83.8 |
| Linoleic acid (C18:2) | 7.9 |
| Linolenic acid (C18:3) | 0.1 |
| Arachidic acid (C20:0) | 0.3 |
| Behenic acid (C22:0) | 0.3 |

Example 1 ($CuO/Al_2O_3$)

16.1836 g of crude diol and 0.1646 g of $CuO/Al_2O_3$(CuO 13% w/w Sigma-Aldrich; CuO content estimated by XRF analysis: 18.8%) were charged into an autoclave pressurised with 25 bar of O2.

The autoclave was held at a temperature of 80° C. for 5 hours with stirring at 500 rpm. At the end of the reaction time the catalyst was separated from the oily phase by centrifuging at 4500 rpm for 10 minutes. Under these operating conditions 3.29 g of pelargonic acid and 5.15 g of azelaic acid were obtained, corresponding to a yield of 55.7% by weight and 66.2% by weight respectively with respect to what could be theoretically obtained.

Example 2 ($CuO/SiO_2$)

The support, $SiO_2$ (Grace, grade 360, AA=600 m²/g, 30-100 μm), was used as such to synthesise the catalyst using the incipient wetness impregnation (IWI) technique: 4.0032 g of support were impregnated with 8.5 mL of a 0.59 M solution of $Cu(NO_3)_2.3H_2O$ (Merk PCode 1027530250, 99.5% purity, MM=241.60 g/mol). The solid was dried in air at 85° C. for 2 hours and then calcined at 300° C. for 3 hours in a flow of air using a temperature gradient of 2° C./min. The CuO content estimated by XRF analysis amounted to 10.50%.

The oxidative cleavage test was carried out in accordance with the procedure described in the above examples charging 15.6813 g of crude diol and 0.1598 g of $CuO/SiO_2$ into an autoclave. 2.34 g of pelargonic acid and 3.64 g of azelaic acid were obtained, corresponding to an approximate yield by weight of 40% of pelargonic acid and 48% of azelaic acid with respect to what could be theoretically obtained.

Example 3 ($CuFe_2O_4$)

An aqueous solution containing 100 mL of $Fe(NO_3)_3.9H_2O$ (1 M) and 50 mL of $Cu(NO_3)_2.2.5H_2O$ (0.5 M) were placed in a separating funnel and added slowly dropwise to 0.5 L of 2 M solution of NaOH with stirring (approximately 500 rpm), held at a constant temperature of 50° C.

The drip rate, approximately one drop a second, was held constant throughout the time of the reaction, while pH was controlled by adding 6 M NaOH in such a way as to keep it at a value above 13. The precipitate formed in this way was allowed to "digest" for two hours with constant stirring and was recovered by filtration under vacuum using a Buchner filter. It was then washed with 1.5 L of demineralised water to remove the sodium and nitrate ions released during the precipitation process.

Finally the solid obtained was dried in air at 120° C. for 12 hours and subsequently calcined at 450° C. for 8 hours in a flow of air using a temperature gradient of 10° C./min.

16.0020 g of crude diol and 0.1631 g of $CuFe_2O_4$ prepared in this way were charged into an autoclave pressurised with 25 bar of O2. The autoclave was held at a temperature of 80° C. for 5 hours with stirring at 500 rpm.

At the end of the reaction time the catalyst was separated from the oily phase by centrifuging at 4500 rpm for 10 minutes.

Under these operating conditions 2.76 g of pelargonic acid and 4.40 g of azelaic acid were obtained, corresponding to an approximate yield by weight of 46.65% of pelargonic acid and 57.24% of azelaic acid with respect to what could be theoretically obtained.

Example 4 ($Cu_{0.6}Fe_{2.4}O_4$)

A copper ferrite was prepared according to the method described in Ex. 3 (Cu/Fe atomic ratio of 1/4).

After calcination, the prepared 6.0 g of $CuFe_2O_4$ and 600.0 g of crude diol were charged into an autoclave provided with stirring system.

The temperature was increased to about 72° C. and the reactor was brought to a pressure of 20 bar with air. The air was continuously fluxed to provide a sufficient supply of oxygen. The oxidative cleavage reaction was stopped after 6 h and 30 minutes.

The reaction product contained about 136 g of pelargonic acid and 183 g of azelaic acid, corresponding to an approximate yield by weight of 58% of pelargonic acid and 60% of azelaic acid with respect to theoretical yield.

Example 5 Comparative ($CuOH/Al_2O_3$)

The support, $Al_2O_3$(Sigma, AA=257 m²/g), calcined at 500° C. for 8 h was used to synthesise the catalyst. 2.0002 g of support were added to 60 mL of solution containing 0.3165 g of $CuCl_2.2H_2O$ (Fluka, 97% wt. purity) and stirred at 500 rpm. NaOH was added until a basic environment was obtained; the precipitated solid was washed with demineralized water and dried overnight at 120° C. The CuOH content estimated by XRD analysis amounted to 10% wt.

The oxidative cleavage test was carried out in accordance with the procedure described in the above examples charging about 15.1173 g of crude diol and 0.1528 g of CuOH/$Al_2O_3$ into an autoclave. Approximate yields by weight of 25.7% of pelargonic acid and 32.3% of azelaic acid were obtained after 5 h, i.e. both about 50% lower than those obtained with CuO/$Al_2O_3$.

The invention claimed is:

1. Process for the preparation of carboxylic acids comprising
subjecting to oxidative cleavage compounds having substituted or non-substituted, linear or branched, saturated or unsaturated alkyl chains containing at least a vicinal diol or epoxide in the presence of an oxidizing agent comprising molecular oxygen and a heterogeneous catalyst consisting of a copper oxide in supported form, a copper ferrite or solid solutions between two metal oxides of Cu and Fe of variable composition or a mixture thereof, wherein the support of said copper oxide is selected from the group consisting of: alumina, silica, $CeO_2$, $TiO_2$ and a mixture of two or more thereof.

2. Process according to claim 1 wherein the said vicinal diol or epoxide is prepared starting from unsaturated fatty acids or derivatives thereof.

3. Process according to claim 2 wherein the said derivatives are esters of unsaturated carboxylic acids with mono-alcohols and/or poly-alcohols.

4. Process according to claim 3 wherein the said derivatives are selected from methyl esters, ethyl esters, propyl esters, butyl esters, monoglycerides, diglycerides, triglycerides or their mixtures.

5. Process according to claim 1 comprising, before the said oxidative cleavage reaction, a step of preparing the said vicinal diol or epoxide by oxidation of unsaturated compounds with an oxidizing agent and a catalyst activating the oxidation reaction of the olefinic double bond.

6. Process according to claim 1, wherein the copper ferrite as a Cu/Fe atomic ratio of 1/2 or below.

7. Process according to claim 1, wherein the support of said copper oxide is alumina, silica or mixture thereof.

* * * * *